(12) United States Patent
Ishida et al.

(10) Patent No.: US 7,923,585 B2
(45) Date of Patent: Apr. 12, 2011

(54) MENTHOL DERIVATIVE AND COOLING AGENT COMPOSITION COMPRISING THE SAME

(75) Inventors: Kenya Ishida, Kanagawa (JP); Takashi Aida, Kanagawa (JP); Hiroyuki Matsuda, Kanagawa (JP); Fumihiro Yanaka, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 375 days.

(21) Appl. No.: 11/628,086

(22) PCT Filed: May 31, 2004

(86) PCT No.: PCT/JP2005/010282
§ 371 (c)(1),
(2), (4) Date: Nov. 30, 2006

(87) PCT Pub. No.: WO2005/115325
PCT Pub. Date: Aug. 12, 2005

(65) Prior Publication Data
US 2007/0225378 A1    Sep. 27, 2007

(30) Foreign Application Priority Data

May 31, 2004 (JP) .................. 2004-161768

(51) Int. Cl.
*C07C 43/00* (2006.01)
*A61K 9/00* (2006.01)
*A61K 8/02* (2006.01)

(52) U.S. Cl. ......... 568/666; 568/670; 424/400; 424/401
(58) Field of Classification Search ................. 568/666, 568/670; 424/400, 401
See application file for complete search history.

(56) References Cited

U.S. PATENT DOCUMENTS

| | | | | |
|---|---|---|---|---|
| 6,328,982 | B1 * | 12/2001 | Shiroyama et al. | 424/401 |
| 6,359,168 | B1 * | 3/2002 | Frerot et al. | 560/186 |
| 6,956,139 | B2 * | 10/2005 | Green et al. | 568/666 |

FOREIGN PATENT DOCUMENTS

| | | |
|---|---|---|
| EP | 1 122 233 A1 | 2/2001 |
| EP | 1 253 130 A2 | 10/2002 |
| GB | 1315626 * | 11/1974 |
| JP | 47-16647 | 9/1972 |
| JP | 47-16648 | 9/1972 |
| JP | 48-33069 | 5/1973 |
| JP | 58-88334 | 5/1983 |
| JP | 61-194049 | 8/1986 |
| JP | 2-290827 | 11/1990 |
| JP | 5-255186 | 10/1993 |
| JP | 5-255217 | 10/1993 |
| JP | 6-65023 | 3/1994 |
| JP | 7-82200 | 3/1995 |
| JP | 7-118119 | 5/1995 |
| WO | WO 03/074622 A1 | 9/2003 |

* cited by examiner

*Primary Examiner* — Sikarl A Witherspoon
(74) *Attorney, Agent, or Firm* — McDmermott Will & Emery LLP

(57) ABSTRACT

The invention relates to innovative menthol derivatives which are represented by the general formula (I) below and are excellent in a cooling effect and cool retaining effect, cooling agent compositions comprising the menthol derivatives, and sensory stimulation agent compositions containing the cooling agent compositions, as well as fragrance compositions, beverage or food products, cosmetic products, toiletry products, bathing agents, and pharmaceutical products containing the cooling agent compositions or sensory stimulation agent compositions. (general formula (I)) wherein R<1> represents a hydrogen atom, an alkyl group having 1 to 4 carbon atoms, or an acyl group having 1 to 5 carbon atoms; R<2> and R<3> independently represent an alkylene group having 2 to 5 carbon atoms and optionally having a substituent; double dotted line represents a single bond or a double bond; and n is an integer of 1 to 3.

12 Claims, No Drawings

MENTHOL DERIVATIVE AND COOLING AGENT COMPOSITION COMPRISING THE SAME

RELATED APPLICATIONS

This application is the U.S. National Phase under 35 U.S.C. §371 of International Application No. PCT/JP2005/010282 filed on May 30, 2005, which in turn claims the benefit of Japanese Patent Application No 2004-161768 filed on May 31, 2004.

TECHNICAL FIELD

The invention relates to innovative menthol derivatives and cooling agent compositions comprising the menthol derivatives. Further, the invention relates to sensory stimulation agent compositions containing the cooling agent composition as well as fragrance compositions, beverage or food products, cosmetic products, toiletry products, bathing agents or pharmaceutical products containing the cooling agent composition or sensory stimulation agent.

BACKGROUND ART

Conventionally, cooling agents giving refreshing feeling (cool and refreshing feeling) and cool feeling (chilly and refreshing feeling), that is cooling effect, to the skin, the mouth, the nose, and the throat of a human being have been used for tooth pastes, confections (e.g. chewing gum, candy and the like), tobacco, poultices, and cosmetics. As a flavor substance giving such cool and refreshing feeling or chilly and refreshing feeling, l-menthol (L-menthol) has been used widely. However l-menthol has such faults that the cooling effect is insufficient in retainability and when the use amount thereof is increased, the cooling effect is strengthened but it is accompanied with adverse bitter taste.

As the compounds having a cooling effect there have been proposed and practically used a large number of compounds other than l-menthol. Examples of the conventionally proposed compounds having the cooling effect other than l-menthol include 3-substituted-p-menthane (e.g. reference to Japanese Patent Application Laid-Open No. 47-16647), N-substituted-p-menthane-3-carboxamide (e.g. reference to Japanese Patent Application Laid-Open No. 47-16648), 1-menthylglucoside (e.g. reference to Japanese Patent Application Laid-Open No. 48-33069), 3-(l-menthoxy)propane-1,2-diol (e.g. reference to Japanese Patent Application Laid-Open No. 58-88334), l-menthyl-3-hydroxybutylate (e.g. reference to Japanese Patent Application Laid-Open No. 61-194049), 1-alkoxy-3-(l-menthoxy)propane-2-ol (e.g. reference to Japanese Patent Application Laid-Open No. 2-290827), esters of 3-hydroxymethyl-p-menthane (e.g. reference to Japanese Patent Application Laid-Open No. 5-255186), N-acetylglycinementhane methyl ester (e.g. reference to Japanese Patent Application Laid-Open No. 5-255217), (−)-isopulegol (e.g. reference to Japanese Patent Application Laid-Open No. 6-65023), (2S)-3-{(1R,2S,5R)-[5-methyl-2-(1-methylethyl)cyclohexyl]-oxy}-1,2-propanediol (e.g. reference to Japanese Patent Application Laid-Open No. 7-82200), and 2-hydroxymenthylmenthol (e.g. reference to Japanese Patent Application Laid-Open No. 7-118119).

The above-mentioned conventionally proposed cooling agents have cooling effect to some extents, but they are insufficient and unsatisfactory in the retainability of the cooling effect. Also, it is required to improve the sensory stimulating effect.

Accordingly, the object of the invention is to provide innovative menthol derivatives excellent in retainability of cool and refreshing feeling or chilly and refreshing feeling without giving undesirable stimulation, peculiar odor, and bitter taste and usable for cooling agents and sensory stimulation agents.

Also, the object of the invention is to provide cooling agent compositions comprising the innovative menthol derivatives and sensory stimulation agent compositions containing the cooling agent compositions.

Further, the object of the invention is to provide fragrance compositions, beverage or food products, cosmetic products, toiletry products, bathing agents, or pharmaceutical products containing the cooling agent composition or sensory stimulation agent.

Inventors of the invention have made various investigations concerning the cooling effect of various kinds of compounds derived from l-menthol to solve the above-mentioned problems, and have found that the menthol derivatives represented by the following general formula (I) have strong cooling effect and are excellent in retainability of the effects and thus useful for cooling substances and sensory stimulation substances as well. Additionally, inventors have also found that in the case l-menthol is used as a cooling agent, the stimulating odor of l-menthol can be moderated by the menthol derivatives, and with respect to fragrance compositions containing the cooling agent compositions comprising the menthol derivatives represented by the following general formula (I), the fragrance note and remnant fragrance of the fragrance compositions is heightened and the fragrance compositions give high fragrance-improving effects to products mixed with the fragrance compositions. The invention was accomplished based on these findings.

DISCLOSURE OF THE INVENTION

The invention relates to the following cooling agent compositions described in any one of items (1) to (4) below.

(1) A cooling agent composition comprising at least one of the menthol derivatives represented by the general formula (I):

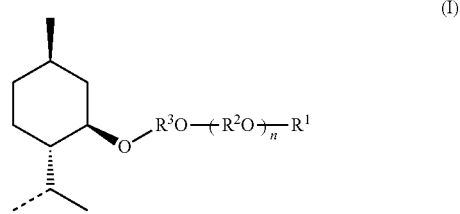

wherein $R^1$ represents a hydrogen atom, an alkyl group having 1 to 4 carbon atoms, or an acyl group having 1 to 5 carbon atoms; $R^2$ and $R^3$ independently represent an alkylene group having 2 to 5 carbon atoms and optionally having a substituent; double dotted line represents a single bond or a double bond; and n is an integer of 1 to 3.

(2) A cooling agent composition according to the item (1) wherein $R^1$ in the general formula (I) is a hydrogen atom.

(3) A cooling agent composition according to the item (1) or (2) wherein at least one kind of cooling substances selected from cooling substances other than the menthol derivatives represented by the general formula (I) is used in combination.

(4) A cooling agent composition according to the item (3) wherein the cooling substance other than the menthol derivatives defined by the general formula (I) include menthol, methane, camphor, pulegol, isopulegol, cineol, Japanese mint oil, peppermint oil, spearmint oil, eucalyptus oil, 3-l-menthoxypropane-1,2-diol, N-alkyl-p-menthane-3-carboxamide, 3-l-menthoxy-2-methylpropane-1,2-diol, p-menthane-3,8-diol, 2-l-menthoxyethane-1-ol, 3-l-menthoxypropane-1- ol, 4-l-menthoxybutane-1-ol (menthyl 3-hydroxybutanate), menthyl lactate, menthol glycerin ketal, and N-methyl-2,2-isopropylmethyl-3-methylbutanamide.

Further the invention relates to the following sensory stimulation agent compositions described in any one of items (5) to (7) below.

(5) A sensory stimulation agent composition containing the cooling agent composition according to any one of the items (1) to (4).

(6) A sensory stimulation agent composition according to the item (5) wherein at least one kind of warming and/or pungent substances is used in combination.

(7) A sensory simulation agent composition according to the item (6) wherein the warming and/or pungent substances are vanillyl ethyl ether, vanillyl propyl ether, vanillin propylene glycol acetal, ethylvanillin propylene glycol acetal, capsaicin, gingerol, vanillyl butyl ether, 4-(l-menthoxymethyl)-2-phenyl-1,3-dioxolane, 4-(l-menthoxymethyl)-2-(3',4'-dihydroxyphenyl)-1,3-dioxolane, 4-(l-menthoxymethyl)-2-(2'-hydroxy-3'-methoxyphenyl)-1,3-dioxolane, 4-(l-menthoxymethyl)-2-(4'-methoxyphenyl)-1,3-dioxolane, 4-(l-menthoxymethyl)-2-(3',4'-methylenedioxyphenyl)-1,3-dioxolane, 4-(l-menthoxymethyl)-2-(3'-methoxy-4'-hydroxyphenyl)-1,3-dioxolane, cayenne pepper oil, cayenne pepper oleoresin, ginger oleoresin, nonylic acid vanillylamide, jambu oleoresin, zanthoxylum extract, sanshool I, sanshool II, zanthoxylum armatamide, black pepper extract, chavicine, piperine, and spilanthole.

Furthermore, the invention relates to a fragrance composition, a beverage or food product, a cosmetic product, a toiletry product, a bathing agent, or a pharmaceutical product described in item (8) or (9) and production methods thereof described in items (10) and (11) below.

(8) A fragrance composition containing 0.01 to 90% by mass of the sensory stimulation agent composition according to any one of the items (5) to (7).

(9) A beverage or food product, a cosmetic product, a toiletry product, a bathing agent, or a pharmaceutical product containing 0.0001 to 50% by mass of the sensory stimulation agent composition according to any one of the items (5) to (7).

(10) A production method of a fragrance composition, a beverage or food product, a cosmetic product, a toiletry product, a bathing agent, or a pharmaceutical product by adding the sensory stimulation agent composition according to any one of the items (5) to (7).

(11) A menthol derivative represented by the general formula (I):

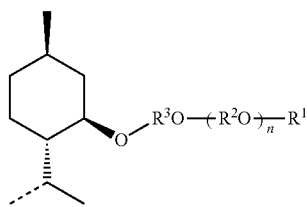

(I)

wherein $R^1$ represents a hydrogen atom, an alkyl group having 1 to 4 carbon atoms, or an acyl group having 1 to 5 carbon atoms; $R^2$ and $R^3$ independently represent an alkylene group having 2 to 5 carbon atoms and optionally having a substituent; double dotted line represents a single bond or a double bond; and n is an integer of 1 to 3.

(12) A menthol derivative according to the item (11) wherein $R^1$ in the general formula (I) is a hydrogen atom.

DETAILED EXPLANATION OF THE INVENTION

Hereinafter, the invention will be described more in detail.

In the menthol derivatives of the invention represented by the above-mentioned general formula (I), $R^1$ represents a hydrogen atom, an alkyl group having 1 to 4 carbon atoms, or an acyl group having 1 to 5 carbon atoms; $R^2$ and $R^3$ independently represent an alkylene group having 2 to 5 carbon atoms and optionally having a substituent; double dotted line represents a single bond or a double bond; and n is an integer of 1 to 3.

In the case $R^1$ represents an alkyl group having 1 to 4 carbon atoms, examples of the alkyl group having 1 to 4 carbon atoms include a methyl group, an ethyl group, a n-propyl group, an isopropyl group, a n-butyl group, an isobutyl, a sec-butyl group, and a tert-butyl group.

In the case $R^1$ represents an acyl group having 1 to 5 carbon atoms, examples of the acyl group having 1 to 5 carbon atoms include a formyl group, an acetyl group, a propionyl group, a butyroyl group, an isobutyroyl group, a valeroyl group, an isovaleroyl group, and a pivaloyl group.

In the case $R^2$ and $R^3$ independently represent an alkylene group having 2 to 5 carbon atoms and optionally having a substituent, examples of the alkylene group having 2 to 5 carbon atoms include an ethylene group, a propylene group, a butylene group and a pentylene group and the substituent is not particularly limited unless it causes any adverse effects in the invention, and examples of the substituent include an alkyl group having 1 to 4 carbon atoms (e.g. methyl, ethyl, n-propyl, isopropyl, n-butyl, isobutyl, sec-butyl, and tert-butyl groups), a hydroxyl group, an alkoxyl group having 1 to 4 carbon atoms (e.g. methoxy, ethoxy, n-propoxy, isopropoxy, n-butoxy, isobutoxy, sec-butoxy, and tert-butoxy groups), an acyl group having 1 to 5 carbon atoms (e.g. formyl, acetyl, propionyl, butyroyl, isobutyroyl, valeroyl, isovaleroyl, and pivaloyl groups), and an acyloxy group having 1 to 5 carbon atoms (e.g. formyloxy, acetyloxy, propionyloxy, butyroyloxy, isobutyroyloxy, valeroyloxy, isovaleroyloxy, and pivaloyloxy groups).

Practical examples of the compounds of the invention represented by the above-mentioned general formula (I) include 2-(2-menthyloxyethoxy)ethanol, 2-(2-menthyloxyethoxy)ethyl methyl ether, 2-(2-menthyloxyethoxy)ethyl ethyl ether, 2-(2-menthyloxyethoxy)ethyl n-propyl ether, 2-(2-menthyloxyethoxy)ethyl isopropyl ether, 2-(2-menthyloxyethoxy)ethyl n-butyl ether, 2-(2-menthyloxyethoxy)ethyl isobutyl ether, 2-(2-menthyloxyethoxy)ethyl sec-butyl ether, 2-(2-menthyloxyethoxy)ethyl tert-butyl ether, 3-(2-menthyloxyethoxy)propanol, 3-(2-menthyloxyethoxy)propyl methyl ether, 3-(2-menthyloxyethoxy)propyl ethyl ether, 3-(2-menthyloxyethoxy)propyl n-propyl ether, 3-(2-menthyloxyethoxy)propyl isopropyl ether, 3-(2-menthyloxyethoxy)propyl n-butyl ether, 3-(2-menthyloxyethoxy)propyl isobutyl ether, 3-(2-menthyloxyethoxy)propyl sec-butyl ether, 3-(2-menthyloxyethoxy)propyl tert-butyl ether, 4-(2-menthyloxyethoxy)butanol, 4-(2-menthyloxyethoxy)butyl methyl ether, 4-(2-menthyloxyethoxy)butyl ethyl ether, 4-(2-menthyloxyethoxy)butyl n-propyl ether, 4-(2-menthyloxyethoxy)butyl isopropyl ether, 4-(2-menthyloxyethoxy)butyl n-butyl ether, 4-(2-menthyloxyethoxy)butyl isobutyl ether, 4-(2-menthyloxyethoxy)butyl sec-butyl ether, 4-(2-menthyloxyethoxy)butyl tert-butyl ether, 2-(3-menthyloxypropoxy)ethanol, 2-(3-menthyloxypropoxy)ethyl methyl ether, 2-(3-menthyloxypropoxy)ethyl ethyl ether, 2-(3-menthyloxypropoxy)ethyl n-propyl ether, 2-(3-menthyloxypropoxy)ethyl isopropyl ether, 2-(3-menthyloxypropoxy)ethyl n-butyl ether, 2-(3- menthyloxypropoxy)ethyl isobutyl ether, 2-(3-menthyloxypropoxy)ethyl sec-butyl ether, 2-(3-menthyloxypropoxy)ethyl tert-butyl ether, 3-(3-menthyloxypropoxy)propanol, 3-(3-menthyloxypropoxy) propyl methyl ether, 3-(3-menthyloxypropoxy)propyl ethyl ether, 3-(3-menthyloxypropoxy)propyl n-propyl ether, 3-(3-menthyloxypropoxy)propyl isopropyl ether, 3-(3-menthyloxypropoxy)propyl n-butyl ether, 3-(3-menthyloxypropoxy)propyl isobutyl ether, 3-(3-menthyloxypropoxy)propyl sec-butyl ether, 3-(3-menthyloxypropoxy)propyl tert-butyl ether, 3-(3-menthyloxy-2-propyl)-2-propanol, 3-(3-menthyloxy-2-propyl)-2-propyl methyl ether, 3-(3-menthyloxy-2-propyl)-2-propyl ethyl ether, 3-(3-menthyloxy-2-propyl)-2-propyl n-propyl ether, 3-(3-menthyloxy-2-propyl)-2-propyl isopropyl ether, 3-(3-menthyloxy-2-propyl)-2-propyl n-butyl ether, 3-(3-menthyloxy-2-propyl)-2-propyl isobutyl ether, 3-(3-menthyloxy-2-propyl)-2-propyl sec-butyl ether, 3-(3-menthyloxy-2-propyl)-2-propyl tert-butyl ether, 2-(2-isopulegyloxyethoxy)ethanol, 2-(2-isopulegyloxyethoxy)ethyl methyl ether, 2-(2-isopulegyloxyethoxy)ethyl ethyl ether, 2-(2-isopulegyloxyethoxy)ethyl n-propyl ether, 2-(2-isopulegyloxyethoxy)ethyl isopropyl ether, 2-(2-isopulegyloxyethoxy)ethyl n-butyl ether, 2-(2-isopulegyloxyethoxy)ethyl isobutyl ether, 2-(2-isopulegyloxyethoxy)ethyl sec-butyl ether, 2-(2-isopulegyloxyethoxy)ethyl tert-butyl ether, 3-(2-isopulegyloxyethoxy)propanol, 3-(2-isopulegyloxyethoxy)propyl methyl ether, 3-(2-isopulegyloxyethoxy)propyl ethyl ether, 3-(2-isopulegyloxyethoxy)propyl n-propyl ether, 3-(2-isopulegyloxyethoxy)propyl isopropyl ether, 3-(2-isopulegyloxyethoxy)propyl n-butyl ether, 3-(2-isopulegyloxyethoxy) propyl isobutyl ether, 3-(2-isopulegyloxyethoxy)propyl sec-butyl ether, 3-(2-isopulegyloxyethoxy)propyl tert-butyl ether, 4-(2-isopulegyloxyethoxy)butanol, 4-(2-isopulegyloxyethoxy)butyl methyl ether, 4-(2-isopulegyloxyethoxy) butyl ethyl ether, 4-(2-isopulegyloxyethoxy)butyl n-propyl ether, 4-(2-isopulegyloxyethoxy)butyl isopropyl ether, 4-(2-isopulegyloxyethoxy)butyl n-butyl ether, 4-(2-isopulegyloxyethoxy)butyl isobutyl ether, 4-(2-isopulegyloxyethoxy) butyl sec-butyl ether, 4-(2-isopulegyloxyethoxy)butyl tert-butyl ether, 2-(3-isopulegyloxypropoxy)ethanol, 2-(3-isopulegyloxypropoxy)ethyl methyl ether, 2-(3-isopulegyloxypropoxy)ethyl ethyl ether, 2-(3-isopulegyloxypropoxy)ethyl n-propyl ether, 2-(3-isopulegyloxypropoxy)ethyl isopropyl ether, 2-(3-isopulegyloxypropoxy)ethyl n-butyl ether, 2-(3-isopulegyloxypropoxy)ethyl isobutyl ether, 2-(3-isopulegyloxypropoxy)ethyl sec-butyl ether, 2-(3-isopulegyloxypropoxy)ethyl tert-butyl ether, 3-(3-isopulegyloxypropoxy)propanol, 3-(3-isopulegyloxypropoxy)propyl methyl ether, 3-(3-isopulegyloxypropoxy)propyl ethyl ether, 3-(3-isopulegyloxypropoxy)propyl n-propyl ether, 3-(3-isopulegyloxypropoxy)propyl isopropyl ether, 3-(3-isopulegyloxypropoxy)propyl n-butyl ether, 3-(3-isopulegyloxypropoxy)propyl isobutyl ether, 3-(3-isopulegyloxypropoxy)propyl sec-butyl ether, 3-(3-isopulegyloxypropoxy)propyl tert-butyl ether, 3-(3-isopulegyloxy-2-propyl)-2-propanol, 3-(3-isopulegyloxy-2-propyl)-2-propyl methyl ether, 3-(3-isopulegyloxy-2-propyl)-2-propyl ethyl ether, 3-(3-isopulegyloxy-2-propyl)-2-propyl n-propyl ether, 3-(3-isopulegyloxy-2-propyl)-2-propyl isopropyl ether, 3-(3-isopulegyloxy-2-propyl)-2-propyl n-butyl ether, 3-(3-isopulegyloxy-2-propyl)-2-propyl isobutyl ether, 3-(3-isopulegyloxy-2-propyl)-2-propyl sec-butyl ether, and 3-(3-isopulegyloxy-2-propyl)-2-propyl tert-butyl ether.

Particularly preferable compounds as the cooling substance or the sensory stimulation substance among the above exemplified compounds are 2-(2-menthyloxyethoxy)ethanol and 3-(3-menthyloxy-2-propyl)-2-propanol.

The menthol derivatives of the invention represented by the general formula (I) are innovative compounds which are not known before.

The compounds of the invention represented by the general formula (I), for example, 2-(2-menthyloxyethoxy)ethanol, can be synthesized by the following method. That is, menthol which is a commercialized product and ethylene oxide are reacted with each other using Lewis acid as a catalyst to obtain menthoxyethanol and then after leaving group is introduced into the alcohol site of the obtained compound, the resulting compound was reacted with ethylene glycol to obtain the exemplified compound. Also, 2-(2-menthyloxyethoxy)ethanol alkyl ethers can be produced by reaction with corresponding alcohols.

As the above-mentioned Lewis acid, for example, anhydrous aluminum chloride, zinc chloride, zinc bromide, iron (III) chloride, and boron trifluoride-diethyl ether complex are exemplified and anhydrous aluminum chloride and zinc chloride are preferable. The amount of the Lewis acid is preferably 0.01 to 3.0 moles and more preferably 0.1 to 1.0 mole to 1 mole of the menthol. The ratio of ethylene oxide to menthol is preferably ethylene oxide 0.1 to 5.0 moles, more preferably 0.5 to 2.5 moles to 1 mole of the menthol. The reaction temperature is generally from −50° C. to 100° C., preferably from −30° C. to 40° C. and the reaction may be carried out, for example, for 1 to 5 hours. Introduction of the leaving group into the obtained menthoxyethanol can be carried out by reaction with methanesulfonyl chloride at −20 to 30° C. reaction temperature for 10 minutes to 20 hours in the presence of a base such as triethylamine. Next, the obtained menthoxyethanol derivative having the leaving group is reacted with ethylene glycol at 20 to 120° C. reaction temperature for 30 minutes to 30 hours to obtain the above-mentioned compound, 2-(2-menthyloxyethoxy)ethanol.

Further, 2-(2-menthyloxyethoxy)ethanol alkyl ether can be produced by reaction of 2-(2-menthyloxyethoxy)ethanol and an alcohol having an alkyl group to be introduced as an ether group.

Other menthol derivatives of the invention represented by the general formula (I) are also produced in similar manner to the manner of producing 2-(2-menthyloxyethoxy) ethanol.

Without producing 2-(l-menthoxy)ethanols as intermediate products, one-step reaction of l-menthol and 1,2-epoxy alkanes may be carried out to produce the menthol derivatives represented by the general formula (I). In such a case, other than the above-mentioned Lewis acid catalyst, a basic catalyst such as Na, K, Li, NaH, KOH, or NaOH may be used preferably. The aimed compound can be isolated from addition polymers of 1,2-epoxyalkanes. Among the basic catalyst, Na and NaH are further preferable in terms of the conversion efficiency and yield.

The amount of the basic catalyst is preferably 0.1 to 3.0 moles, more preferably 0.5 to 1.5 moles to 1 mole of the l-menthol that is a raw material compound (a substrate). If the amount of the base is less than 0.1 mole, it becomes difficult to smoothly produce the aimed product and if it exceeds 1.5 moles, the yield and conversion ratio is not improved to result in disadvantage in the cost.

Thus obtained menthol derivatives represented by the general formula (I) and obtained in such a manner have strong and retainable cooling effect and can be used solely for a cooling agent or a sensory stimulation agent as it is.

It is required to change the applicable scope and applicable methods of the menthol derivatives of the invention depending on the types of the products and use purposes, and in general, it is preferable to use them in a concentration of 0.0001 to 20% by mass, particularly 0.001 to 5% by mass, in the whole composition of a product.

Cooling agent compositions or sensory stimulation agent compositions with heightened cool feeling intensity can be produced by use of at least one kind of cooling substances which are excluded from the menthol derivatives of the invention in combination with the menthol derivatives of the invention.

The cooling substances excluded from the menthol derivatives of the invention include, for example, menthol, menthone, camphor, pulegol, isopulegol, cineole, Japanese mint oil, peppermint oil, spearmint oil, eucalyptus oil, 3-l-menthoxypropane-1,2-diol, N-alkyl-p-menthane-3-carboxamide, 3-l-menthoxy-2-methylpropane-1,2-diol, p-menthane-3,8-diol, 2-l-menthoxyethan-1-ol, 3-l-menthoxypropan-1-ol, 4-l-menthoxybutan-1-ol (menthyl 3-hydroxybutanate), menthyl lactate, menthol glycerin ketal, and N-methyl-2,2-isopropylmethyl-3-methylbutanamide.

One or more of these compounds may be added and used properly.

The menthol derivatives of the invention and the cooling substances excluded from these menthol derivatives may be used at any optional ratio to an extent of causing no adverse effects of the invention and the use ratio of the menthol derivatives and the cooling substances excluded from them is preferably (1:99) to (70:30) by mass. The cooling agent compositions of the invention may be added to fragrance compositions, food and beverage products, cosmetic products, toiletry products, bathing agents, or pharmaceutical products.

In the invention, since the above-mentioned cooling agent compositions have strong and retainable cooling effect, addition of the cooling agent compositions makes it possible to produce sensory stimulation agent compositions having cooling effect. In the case of producing the sensory stimulation agent compositions, with respect to the mixing amount of the cooling agent compositions, it is required to properly change the applicable scope and applicable methods thereof depending on the types of the products and use purposes, and in general, it is preferable to use them in a concentration of 0.0001 to 20% by mass, particularly 0.001 to 5% by mass, to the whole compositions of the sensory stimulation agent compositions. Additionally, the sensory stimulation agent compositions of the invention are compositions giving effects of stimulating the sensibility. The effects of stimulating the sensibility include cooling effect and warming and/or pungent effect and accordingly, the sensory stimulation agent compositions of the invention include both cooling agent compositions and warming and/or pungent agent compositions.

With respect to the cooling agent compositions of the invention, by using warming and/or pungent substances in combination, the stimulating effects of the sensory stimulation agent compositions can be adjusted. Examples of the warming and/or pungent substances include vanillyl ethyl ether, vanillyl propyl ether, vanillin propylene glycol acetal, ethylvanillin propylene glycol acetal, capsaicin, gingerol, vanillyl butyl ether, 4-(l-menthoxymethyl)-2-phenyl-1,3-dioxolane, 4-(l-menthoxymethyl)-2-(3',4'-dihydroxyphenyl)-1,3-dioxolane, 4-(l-menthoxymethyl)-2-(2'-hydroxy-3'-methoxyphenyl)-1,3-dioxolane, 4-(l-menthoxymethyl)-2-(4'-methoxyphenyl)-1,3-dioxolane, 4-(l-menthoxymethyl)-2-(3',4'-methylenedioxyphenyl)-1,3-dioxolane, 4-(l-menthoxymethyl)-2-(3'-methoxy-4'-hydroxyphenyl)-1,3-dioxolane, cayenne pepper oil, cayenne pepper oleoresin, ginger oleoresin, nonylic acid vanillylamide, jambu oleoresin, zanthoxylum extract, sanshool I, sanshool II, zanthoxylum armatamide, black pepper extract, chavicine, piperine, and spilanthole. One or more of these compounds may be added and used properly.

The mixing ratio of the warming and/or pungent substances and the cooling substances may be to an extent of causing no warming and/or pungent effect of the warming and/or pungent substances by the addition of the warming and/or pungent substance in the case of aiming the cooling effect and it may be 0.001 to 0.95 times as much, preferably 0.01 to 0.5 times as much, in the total amounts of the cooling agent compositions. In this case, with respect to the sensory stimulation agent compositions of the invention, addition of the warming and/or pungent substances at ratios in the above-mentioned range to the cooling agent compositions further improves the cooling effect to result in intensified cooling effect. Also, in the case of aiming the warming and/or pungent effect, mixing ratio of the cooling substances may be to an extent of causing no cooling effect of the cooling substances by their addition and it may be 0.001 to 0.95 times as much, preferably 0.01 to 0.5 times as much, in the total amounts of the warming and/or pungent substances.

In the invention, the cooling agent compositions or the sensory stimulation agent compositions may be added directly to various products such as fragrance compositions, food and beverage products, cosmetic products, toiletry products, bathing agents, and pharmaceutical products. Further the cooling agent compositions or the sensory stimulation agent compositions may be added at first to the fragrance compositions to obtain the fragrance compositions containing the cooling agent compositions or sensory stimulation agent compositions (the fragrance compositions of the invention) and then the fragrance compositions containing the cooling agent compositions or sensory stimulation agent compositions may be added to products. Furthermore menthol derivatives of the invention, cooling agent compositions other than these menthol derivatives, and the warming and/or pungent substances may be added separately to the fragrance compositions.

Examples of fragrance components contained together with the cooling agent compositions or the sensory stimulation agent compositions of the invention include various types of synthesized fragrances, natural essential oils, synthesized essential oils, citrus oils, animal fragrance and the like. For example, there can be used fragrance components in a wide range of the types as described in Collection of Well-known Prior Art (fragrance), vol. 1, Jan. 29, 1999, issued by Japanese Patent Office. Among these, typical components are α-pinene, limonene, cis-3-hexenol, phenylethyl alcohol, styrallyl acetate, eugenol, rose oxide, linalool, benzaldehyde, muscone, Musk T (manufactured by Takasago International Corporation), Tesalon (manufactured by Takasago International Corporation) and the like.

The contents of the cooling agent compositions or the sensory stimulation agent compositions in the fragrance compositions containing the cooling agent compositions or sensory stimulation agent composition may be adjusted properly depending on the types of the fragrance and other components to be mixed together and the purpose of the use of the fragrance compositions containing the cooling agent compositions or sensory stimulation agent composition. For example, in the case of perfume compositions for perfumery products, in general, the contents of the cooling agent compositions or the sensory stimulation agent compositions to the whole amount of the perfume compositions are 0.0001 to 50% by mass, preferably 0.001 to 50% by mass, and particularly preferably 0.01 to 20% by mass.

In the case of the fragrance compositions for food and beverage products, in general, the contents of the cooling agent compositions or the sensory stimulation agent compositions in the whole amount of the fragrance compositions are preferably 0.0001 to 50% by mass and more preferably 0.001 to 30% by mass.

The fragrance compositions containing cooling agent compositions or sensory stimulation agent compositions of the invention may further comprise one or more types of other fragrance retaining agents commonly used in fragrance compositions. The examples of the fragrance retaining agents include ethylene glycol, propylene glycol, dipropylene glycol, glycerin, hexyl glycol, benzyl benzoate, triethyl citrate, diethyl phthalate, hercolyn, middle chain fatty acid triglyceride, middle chain fatty acid diglyceride and the like. One or more of these compounds may be added.

As described, the cooling agent compositions or sensory stimulation agent compositions of the invention may be used solely as the cooling agent compositions or the sensory stimulation agent compositions or in form of the fragrance compositions containing the cooling agent compositions for giving cooling or sensory stimulation to various kinds of products. As the products to which cooling or sensory stimulation can be given by the cooling agent compositions or the sensory stimulation agent compositions of the invention themselves or fragrance compositions containing the cooling agent compositions or sensory stimulation agent compositions, there are exemplified food and beverage products, cosmetic products, toiletry products, bathing agents, pharmaceutical products and the like.

Practical examples of the food and beverage products capable of giving cool feeling or sensory stimulation by the cooling agent compositions or sensory stimulation agent compositions of the invention, or fragrance compositions containing these cooling agent compositions or sensory stimulation agent compositions are not particularly limited and include beverages such as fruit juice beverages, fruit liquors, milk drinks, carbonated beverages, refreshing beverages, and health and nutrient drinks; frozen confectionery such as ice creams, sherbets, and ice-lolly; desserts such as jelly and pudding; confectionery such as cakes, cookies, chocolates, and chewing gum; Japanese confectionery such as buns with bean-jam filling, bars of sweet jellied bean paste, sweet jellied pounded rice; jams; candies; breads; tea beverages and favorite beverages such as green tea, oolong tea, black tea, persimmon leaf tea, Chamomile tea, Sasa veitchii tea, mulberry leaf tea, Houttuynia cordata tea, Puer tea, Mate tea, Rooibos tea, Gimunema tea, Guava tea, coffee, and cocoa; soups such as Japanese flavor soup, western flavor soup, and Chinese flavor soup; seasonings; various instant beverages and foods; various snack foods; compositions for oral use and the like.

Examples of the cosmetic products or daily goods to which the cooling agent compositions, sensory stimulation agent compositions or fragrance compositions containing these cooling agent compositions or sensory stimulation agent compositions give fragrance include fragrance products, basic skin-care cosmetics, make-up cosmetics, hair cosmetics, sunburn cosmetics, medical cosmetics, hair care products, soaps, body washing soaps, agents for bathing, detergents, softening finishing agents, cleaning agents, kitchen detergents, bleaching agents, aerosol agents, deodorants and aromatic agents, repellents, other miscellaneous goods and the like.

More particular examples of the products may include: as fragrance products, perfume, eau de perfume, eau de toilet, eau de cologne, and the like;

as basic skin-care cosmetics, face washing creams, varnishing creams, cleansing creams, cold creams, massage creams, milky lotions, skin toning lotion, cosmetic solution, packs, makeup remover, and the like;

as makeup cosmetics, foundations, face powders, pressed powders, talcum powders, lip sticks, lip creams, cheek powders, eyeliners, mascara, eye shadows, eyebrow pencils, eye packs, nail enamels, nail enamel removers, and the like; as hair care cosmetics, pomades, brilliantine, setting lotions, hair sticks, hair solids, hair oils, hair treatments, hair creams, hair tonics, hair liquids, hair sprays, bandlin, hair restorers, hair dyes, and the like; as sunburn cosmetics, suntan products, sunscreen products, and the like;

as medical cosmetics, antiperspirants, after-shave lotions and gels, permanent wave lotion, medicated soaps, medicated shampoos, medicated skin care products, and the like; as hair care products, shampoos, rinses, shampoo-including-rinse, hair conditioners, hair treatments, hair packs, and the like;

as soaps, toilet soaps, bath soaps, perfumed soaps, transparent soaps, synthetic soaps, and the like;

as body washing soaps, body soaps, body shampoos, hand soaps, and the like;

as agents for bathing, bathing agents (e.g. bath salts, bath tablets, bath liquids, and the like), foam bath (bubble bath and the like), bath oils (e.g. bath perfumes, bath capsules and the like), milk bath, bath gel, bath cubes, and the like; as detergents, heavy duty detergents for clothes, light duty detergents for clothes, liquid detergents, laundering soaps, compact detergents, powder soaps, and the like; as softening finishing agents, softeners, furniture care, and the like;

as cleaning agents, cleansers, house cleaners, toilet cleaning agents, cleaning agents for bath room, glass cleaners, mold removing agents, cleaners for drainage pipes, and the like; as kitchen detergents, soaps for kitchen, synthetic soaps for kitchen, dish cleaners, and the like;

as bleaching agents, oxidizing type bleaching agents (chlorine type bleaching agents, oxygen type bleaching agents, and the like), reducing type bleaching agents (sulfur type bleaching agents and the like), photo-bleaching agents, and the like; as aerosols, spray type and powder spray type aerosols; as deodorants and aromatic agents, solid type, gel type, liquid type agents, and the like;

as other miscellaneous goods, tissue paper, toilet paper, and the like;

as the compositions for oral care, tooth pastes, mouth cleaners, mouth wash, troches, chewing gums, and the like; and as pharmaceutical products, poultices, external skin care pharmaceuticals such as ointments, internal administration medicines, and the like.

In the case the cooling agent compositions, the sensory stimulation agent compositions or the fragrance compositions containing the cooling agent compositions or the sensory stimulation agents compositions of the invention are used for giving such cool feeling or sensory stimulation to the various types of products described above, depending on the types of the products and final states (product states, e.g. liquid phase, solid phase, powder phase, gel state, mist state, aerosol state, or the like) of the products to which the cool feeling or sensory stimulation is supplied, the cooling agent compositions, the sensory stimulation agent compositions or the fragrance compositions containing these cooling agent compositions or sensory stimulation agents compositions may be added or supplied directly to the products; or the cooling agent compositions, the sensory stimulation agent compositions or the fragrance compositions containing the cooling agent compositions or the sensory stimulation agent compositions may be added or supplied in form of liquids by dissolving such compositions in alcohols or polyhydric alcohols such as propylene glycol and glycerin; or they may be added or supplied while being solubilized, emulsification-dispersed, or dispersed by using natural gums such as gum arabic and tragacanth gum, or surfactants (e.g. nonionic surfactants such as glycerin fatty acid esters and saccharide fatty acid esters; anionic surfactants, cationic surfactants, and amphoteric surfactants); or they may be added or supplied while being coated in powder state by using excipient, e.g.

natural gums such as gum arabic, gelatin, and dextrin; or they may be added or supplied while being encapsulated in microcapsules. Further, the cooling agent compositions, the sensory stimulation agent compositions or the fragrance compositions containing the cooling agent compositions or the sensory stimulation agent compositions may be stabilized and controlled release by enclosing the compositions in an enclosing agent such as cyclodextrin.

The addition or supply amounts of the cooling agent compositions or the sensory stimulation agent compositions to the products to be supplied with the cool feeling or sensory stimulation may be adjusted properly depending on the effects and functions of the cool feeling or sensory stimulation which the products are required to have. In general, the addition or supply amounts of the cooling agent compositions or the sensory stimulation agent compositions are preferably about $1 \times 10^{-7}$ to 0.1% by mass and more preferably $1 \times 10^{-6}$ to 0.01% by mass to the mass of the products.

BEST MODE FOR CARRYING OUT THE INVENTION

Hereinafter, the invention will be described more particularly with reference to Examples, but it is not intended that the invention be limited to the described Examples. Modifications and substitutions can be made without departing from the spirit and scope of the invention.

The products of Synthesis examples and Examples were measured by using the following apparatus.

Nuclear Magnetic Resonance Spectrometry:
$^1$H-NMR: AM-400 (400 MHz) manufactured by BRUKER Inc.
External standard substance: tetramethylsilane Gas chromatography (GC):
HP 6890 manufactured by HEWLETT PACKARD Inc.
Column: NEUTRABOND-1 manufactured by GL Sciences Inc. (inner diameter×length=0.25 mm×30 m)
Mass Spectrometry (MS):
M-80 mass spectrometer manufactured by Hitachi Ltd. (ionization voltage 20 eV)

Example 1

Synthesis of 2-(2-l-menthyloxyethyl)ethanol (1) Synthesis of l-menthyloxyethanol

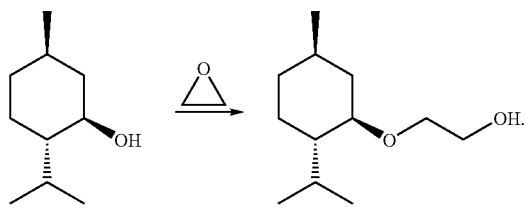

At first, 100.0 g (0.64 mol) of l-menthol and 42.7 g (0.32 mol) of anhydrous aluminum chloride were added into a reaction vessel and after replacement with nitrogen, 500 ml of toluene was further added to the vessel and stirred with the mixture under the ice-cooling condition to cool the resulting mixture to 5° C. And while the temperature of the solution being kept at 5 to 10° C., 57 g of ethylene oxide was further added. On completion of the supply, the mixture was stirred for one more hour at a room temperature to complete the reaction. Next, the reaction solution was cooled again and washed with 150 ml of 10% aqueous hydrochloric acid while being kept at 20° C. or lower. After the reaction solution was washed again with 50 ml of saturated sodium hydrogen carbonate aqueous solution and then with 100 ml of saturated brine, water therein was removed with sodium sulfate and the solvent was recovered under reduced pressure to obtain 123.1 g of crude l-menthyloxyethanol. The obtained product was distilled to isolate and recover 45.7 g of an unreacted raw material, l-menthol, and refine and isolate 60.8 g of an aimed product, l-menthyloxyethanol. Theoretical yield: 47.4% based on l-menthol.

(2) Synthesis of l-menthyloxyethylmethane sulfonate

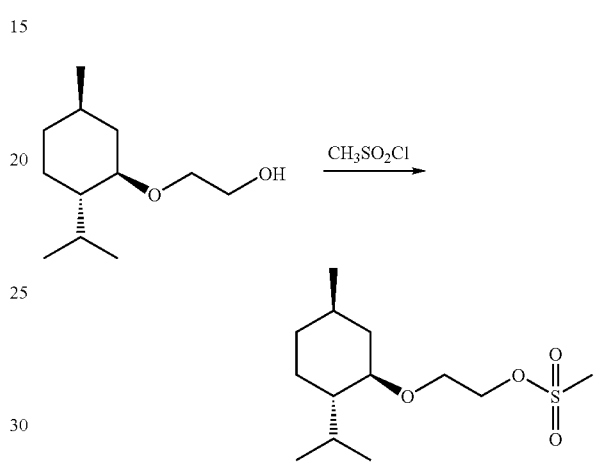

40.0 g (0.2 mole) of the l-menthyloxyethanol obtained as described in (1), 21.2 g (1.05 equivalent) of triethylamine, and 80 ml of toluene were loaded and under the ice-cooling condition (1 to 3° C.), 22.92 g (1.0 equivalent) of methanesulfonyl chloride was dropwise added at 10° C. or lower and after aging at the temperature for 1 hour, the reaction product was mixed with water (80 ml) and separated (pH 8) and washed with 60 ml of an 1% NaHCO$_3$ aqueous solution three times. Under reduced pressure, toluene was recovered to obtain 48.0 g of l-menthoxyethylmethane sulfonate (chemical purity (GC): 97.2%). Yield: 86.2%.

(3) Synthesis of 2-(2-l-menthyloxyethyl)ethanol

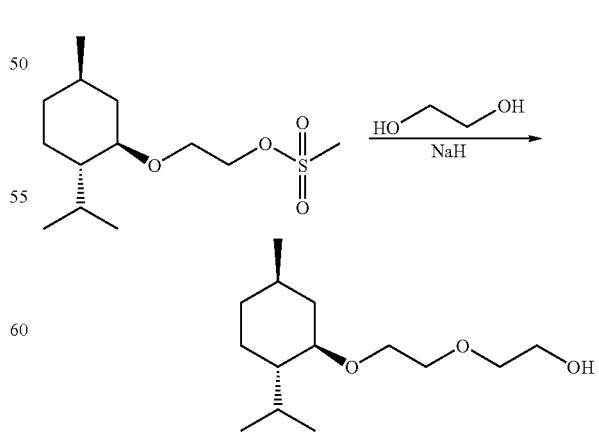

Under the ice-cooling and stirring conditions, a mixture solution of 50 ml of dimethyl formamide (DMF) and 49.6 g (0.8 mmol) of ethylene glycol was dropwise added to a mixture of 4.4 g (0.11 mol) of 60% NaH and 50 ml of DMF under stirring and then the resulting mixture was stirred at a room temperature for 1 hour. Thereafter the mixture was heated to 70 to 74° C., and 50 ml of DMF solution containing 27.8 g (0.1 mole) of the 1-menthyloxyethylmethane sulfonate obtained as described in (2) was dropwise added to the mixture in 50 minutes. After being stirred for 3 hours at this temperature, the reaction mixture was cooled to a room temperature, mixed with 100 ml of diisopropyl ether, and then washed with 50 ml of water three times, and the separated organic layer was concentrated under reduced pressure and then distilled to obtain 21.5 g of diethylene glycol monomenthyl ether (bp: 102-105° C./40 Pa, chemical purity (GC): 98.5%) in form of a colorless and transparent oily substance. Yield: 88.0%.

NMR (δ ppm) 0.77 (3H, d, J=7.0), 0.80-0.99 (9H, m), 1.22-1.25 (1H, m), 1.34 (1H, m), 1.60-1.66 (2H, m), 2.07-2.10 (1H, m), 2.18-2.21 (1H, m), 2.35-2.58 (1H, broad), 3.05-3.10 (1H, m), 3.47-3.49 (1H, m), 3.60-3.62 (2H, m), 3.65-3.67 (2H, m), 3.71-3.73 (2H, m), 3.75-3.82 (1H, m)

MS (m/z): 244 (M+), 229, 214, 201, 187, 173, 159, 138, 123, 107, 95, 83, 69, 45, 41

Example 2

Production of 2-(2-l-menthyloxyethyl)ethanol Using NaH

A four-neck flask of 100 ml capacity equipped with a Dimroth condenser and a thermometer was loaded with 78.0 g (0.5 mole) of l-menthol and 20 g (0.5 mole) of NaH (60%), and after replacement with nitrogen, 160 ml of toluene was added thereto and the mixture was heated, refluxed, and stirred for 2 hours. The resulting reaction solution from which no hydrogen generation was observed was cooled to 60° C. and 44 g (1.0 mole) of ethylene oxide was added at this temperature in 1 hour. After being refluxed and stirred for 2 hours, the reaction solution was again cooled and washed with 100 ml of 1% hydrochloric acid aqueous solution while being kept at 10° C. or lower. Next, after the reaction solution was washed with 50 ml of a saturated sodium hydrogen carbonate aqueous solution and then with 100 ml of saturated brine, water therein was removed with sodium sulfate, and the solvent was recovered under reduced pressure and then distilled to isolate and recover unreacted l-menthol and 2-(l-menthoxy)ethanol and thus obtain 15.6 g of the aimed product, 2-(2-l-menthyloxyethanol)ethanol.

Example 3

Sensory Evaluation

Oral evaluation of an aqueous solution of 2-(2-l-menthyloxyethyl)ethanol obtained in Example 1 in a concentration of 20 ppm was carried out by 7 expert panelists having 5 years or longer experience. Seven expert panelists all evaluated that it had excellent cool and refreshing feeling quality.

Example 4

Synergetic Effect with Menthol

Mixtures of l-menthol and 2-(2-l-menthyloxyethyl) ethanol obtained in Example 1 at 7:3 and 9:1 (ratio by mass) were prepared. 1,000 ml of aqueous solutions containing each obtained mixture in a concentration of 20 ppm were prepared and subjected to the oral evaluation. For comparison, a 20 ppm aqueous solution of l-menthol alone was also subjected to the oral evaluation.

Evaluation was carried out by seven expert panelists having 5 years or longer experience in such a manner that the panelists took each 10 ml of solution in mouth for 10 seconds, discharged the solution and evaluated the intensity of the cool and refreshing feeling quality (refreshing feeling) at that moment, which was defined as 0 second, and further evaluated the retainability of the intensity of the feeling 3 minutes later. The results are shown in Table 1 and Table 2.

TABLE 1

| Intensity comparison results | | | |
|---|---|---|---|
| | Solutions containing mixtures have higher cool and refreshing feeling quality (refreshing feeling) | Solutions containing mixtures have similar cool and refreshing feeling quality (refreshing feeling) | Solution containing menthol alone has higher cool and refreshing feeling quality (refreshing feeling) |
| 7:3 mixture | 6 | 1 | 0 |
| 9:1 mixture | 7 | 0 | 0 |

TABLE 2

| Retainability comparison results | | | |
|---|---|---|---|
| | Solutions containing mixtures have higher retainable cool and refreshing feeling quality | Solutions containing mixtures have similarly retainable cool and refreshing feeling quality | Solution containing menthol alone has higher retainable cool and refreshing feeling quality |
| 7:3 mixture | 5 | 2 | 0 |
| 9:1 mixture | 6 | 1 | 0 |

As shown in Table 1, six panelists among seven answered that the solution containing the 7:3 mixture had higher cool and refreshing feeling quality than that of the solution containing menthol alone. Further, seven panelists all answered that the solution containing the 9:1 mixture had higher cool and refreshing feeling quality than that of the solution containing menthol alone.

As shown in Table 2, five panelists among seven answered that the solution containing the 7:3 mixture had higher retainable cool and refreshing feeling quality than that of the solution containing menthol alone. Further, six panelists among seven answered that the solution containing the 9:1 mixture had higher cool and refreshing feeling quality than that of the solution containing menthol alone.

Being made clear from Example 3 and Example 4, the compound of the invention was evaluated remarkably high in both cases of the compound alone and in combination with menthol.

Example 5

Body Shampoo

A fragrance composition containing the sensory stimulation agent was produced from 35 parts by mass of 2-(2-l- menthyloxyethyl)ethanol obtained in Example 1 and 65 parts by mass of a citrus-herbal blended fragrance manufactured by Takasago International Corporation, and by using the composition, a body shampoo was prepared according to the following prescription. The mixing amount in the prescription was on the basis of part by mass. The body shampoo had cool feeling and retained the cooling effect.

<Prescription of Body Shampoo>

| (Ingredients) | (Mixing amount) |
| --- | --- |
| Triethanolamine | 9.00 |
| Lauric acid | 6.00 |
| Myristic acid | 9.00 |
| Lauryl polyoxyethylenesulfosuccinate disodium salt (1 E.O.) (42%) | 10.00 |
| Alkyl (C8-16) glucoxide | 8.00 |
| Glyceryl laurate | 1.00 |
| 2-hydroxyethyl distearate | 2.50 |
| Coconut oil fatty acid diethanol amide | 3.00 |
| Propylene glycol | 5.00 |
| Dibutylhydroxytoluene | 0.05 |
| Edetic acid disodium salt | 0.10 |
| Ethyl p-oxybenzoate | 0.20 |
| Methyl p-oxybenzoate | 0.10 |
| Fragrance composition containing sensory stimulation agent | 0.95 |
| Purified water | balance |
| Total | 100.00 |

Example 6

Fragrance Composition

The fragrance composition was produced according to the following prescription by an ordinal method. The mixing amount in the prescription was on the basis of part by mass.

<Prescription of Fragrance Composition>

| (Ingredients) | (Mixing amount) |
| --- | --- |
| Apple base (manufactured by Takasago International Corporation) | 8.0 |
| Bergamot oil | 14.0 |
| Ethyl acetoacetate | 5.0 |
| Methyl dihydrojasmonate | 23.0 |
| Laurinal | 3.0 |
| Levosandol (manufactured by Takasago International Corporation) | 4.0 |
| Orange oil | 8.0 |
| 10-oxa-16-hexadecanoride | 8.0 |
| Phenoxanol (manufactured by IFF Inc.) | 6.0 |
| Styrallyl acetate | 3.0 |
| Tesalon (manufactured by Takasago International Corporation) | 8.0 |
| 2-(2-1-menthyloxyethyl)ethanol | 30.0 |

Example 7

Shampoo

According to the following prescription, 100 g of a shampoo was prepared by adding 1.0% of the fragrance composition of Example 5. The shampoo had cool feeling and retained the cooling effect.

<Prescription of Shampoo>

| (Ingredients) | (Mixing amount (g)) |
| --- | --- |
| Sodium polyoxyethylene lauryl ether sulfate | 14.00 |
| Lauric acid amide propyl betaine | 4.00 |
| Coconut oil fatty acid diethanol amide | 3.00 |
| Cationic cellulose | 0.50 |
| Ethylene glycol distearate | 1.00 |
| Ethyl p-oxybenzoate | 0.25 |
| Citric acid | proper quantity |
| Fragrance composition | 1.00 |
| Purified water | balance |
| Total | 100.00 |

Example 8

Transparent Shampoo

According to the following prescription, a transparent shampoo was prepared. It had cool feeling and retained the cooling effect.

<Prescription of Transparent Shampoo>

| (Ingredients) | (Mixing amount (g)) |
| --- | --- |
| Polyquaternium 10 | 10.0 |
| Sodium laureth sulfate (aqueous 30% solution) | 300.0 |
| Lauroylsarcosine sodium salt (aqueous 30% solution) | 50.0 |
| Cocamide propene betaine | 100.0 |
| Coconut fatty acid diethanol amide | 40.0 |
| 1,3-butylene glycol | 20.0 |
| Citric acid | 3.0 |
| Methylparaben | 2.0 |
| Propylparaben | 0.5 |
| Edetic acid disodium salt | 1.0 |
| l-menthol | 6.3 |
| 2-(2-1-menthyloxyethyl)ethanol | 0.6 |
| Vanillyl butyl ether | 0.1 |
| Citrus type fragrance | 3.0 |
| Purified water | balance |
| Total | 1000.0 |

Example 9

Tooth Paste

According to the following prescription, a tooth paste was prepared. The tooth paste had cool feeling and retained the cooling effect.

<Prescription of Tooth Paste>

| (Ingredients) | (Mixing amount (g)) |
| --- | --- |
| l-menthol | 0.25 |
| 2-(2-1-menthyloxyethyl)ethanol | 0.25 |
| Calcium hydrogen phosphate (dihydrate) | 50.00 |
| Glycerin | 25.00 |
| Sodium lauryl sulfate | 1.40 |
| Carboxymethyl cellulose sodium salt | 1.50 |
| Saccharin sodium salt | 0.20 |

-continued

| (Ingredients) | (Mixing amount (g)) |
|---|---|
| Sodium benzoate | 0.10 |
| Strawberry type flavor (manufactured by Takasago International Corporation) | 0.70 |
| Purified water | balance |
| Total | 100.00 |

EFFECT OF INVENTION

The menthol derivatives of the invention are free from undesirable stimulating feeling, peculiar odor or bitter taste and by being added to various food and beverage products, compositions for oral use, and cosmetics, they can give cool and refreshing feeling and chilly and refreshing feeling and are excellent in retainability of such effects. Further, they have excellent properties of scarcely giving skin-irritating feeling undesirable for a human being. They are also excellent in coloration resistance during storage and therefore excellent in stability.

The invention claimed is:

1. A cooling agent composition comprising at least one kind of menthol derivatives represented by the general formula (I):

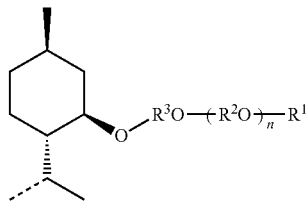

(I)

wherein $R^1$ represents a hydrogen atom;
$R^2$ and $R^3$ independently represent an alkylene group having 2 carbon atoms and optionally having a substituent;
double dotted line represents a single bond or a double bond; and
n is an integer of 1 to 3.

2. A cooling agent composition according to claim 1, wherein at least one kind of cooling substances selected from cooling substances other than the menthol derivatives represented by the general formula (I) is used in combination.

3. A cooling agent composition according to claim 2, wherein the cooling substances other than the menthol derivatives represented by the general formula (I) are menthol, menthone, camphor, pulegol, isopulegol, cineole, Japanese mint oil, peppermint oil, spearmint oil, eucalyptus oil, 3-l-menthoxypropane-1,2-diol, N-alkyl-p-menthane-3-carboxamide, 3-l-menthoxy-2-methylpropane-1, 2-diol, p-menthane-3,8-diol, 2-1-menthoxyethane-1-ol, 3-1-menthoxypropane-1-ol, 4-1-menthoxybutane-1-ol (menthyl 3-hydroxybutanate), menthyl lactate, menthol glycerin ketal, and N-methyl-2,2-isopropylmethyl-3-methylbutanamide.

4. A sensory stimulation agent composition containing the cooling agent composition according to claim 1.

5. A sensory stimulation agent composition containing the cooling agent composition according to claim 2.

6. A sensory stimulation agent composition according to claim 4, wherein at least one kind of warming and/or pungent substances is used in combination.

7. A sensory stimulation agent composition according to claim 5, wherein at least one kind of warming and/or pungent substances is used in combination.

8. A sensory simulation agent composition according to claim 6, wherein the warming and/or pungent substances are vanillyl ethyl ether, vanillyl propyl ether, vanillin propylene glycol acetal, ethylvanillin propylene glycol acetal, capsaicin, gingerol, vanillyl butyl ether, 4-(1-menthoxymethyl)-2-phenyl-1,3-dioxolane, 4-(1-menthoxymethyl)-2-(3',4'-dihydroxyphenyl)-1,3-dioxolane, 4-(1-menthoxymethyl)-2-(2'-hydroxy-3'-methoxyphenyl)-1,3-dioxolane, 4-(1-menthoxymethyl)-2-(4'-methoxyphenyl)-1,3-dioxolane, 4-(1-menthoxymethyl)-2-(3',4'-methylenedioxyphenyl)-1,3-dioxolane, 4-(1-methoxymethyl)-2-(3'-methoxy-4'-hydroxyphenyl)-1,3-dioxolane, cayenne pepper oil, cayenne pepper oleoresin, ginger oleoresin, nonylic vanillylamide, jambu oleoresin, zanthoxylum fruit extract, sanshool I, sanshool II, zanthoxylum armatamide, black pepper extract, chavicine, piperine, and spilanthole.

9. A fragrance composition containing 0.01 to 90% by mass of the sensory stimulation agent composition according to any one of claims 4, 5, or 6.

10. A beverage or food product, a cosmetic product, a toiletry product, a bathing agent, or a pharmaceutical product containing 0.0001 to 50% by mass of the sensory stimulation agent composition according to any one of claims 4, 5, or 6.

11. A production method of a fragrance composition, a beverage or food product, a cosmetic product, a toiletry product, a bathing agent, or a pharmaceutical product by adding the sensory stimulation agent composition according to any one of claims 4, 5, or 6.

12. A menthol derivative represented by the general formula (I):

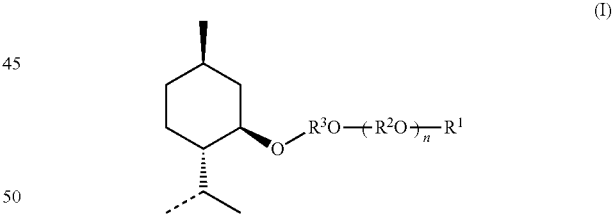

(I)

wherein $R^1$ represents a hydrogen atom;
$R^2$ and $R^3$ independently represent an alkylene group having 2 carbon atoms and optionally having a substituent;
double dotted line represents a single bond or a double bond; and
n is an integer of 1 to 3.

* * * * *

UNITED STATES PATENT AND TRADEMARK OFFICE
CERTIFICATE OF CORRECTION

| | | |
|---|---|---|
| PATENT NO. | : 7,923,585 B2 | |
| APPLICATION NO. | : 11/628086 | |
| DATED | : April 12, 2011 | |
| INVENTOR(S) | : Kenya Ishida et al. | |

It is certified that error appears in the above-identified patent and that said Letters Patent is hereby corrected as shown below:

Title Page, under Section (22) PCT Filed: change from "May 31, 2004" to --May 30, 2005--

Signed and Sealed this
Eighth Day of May, 2012

David J. Kappos
*Director of the United States Patent and Trademark Office*